(12) United States Patent
MacNeal

(10) Patent No.: US 6,290,906 B1
(45) Date of Patent: Sep. 18, 2001

(54) METHOD FOR REMOVING STERILANT FROM OBJECTS SUBJECTED TO GASEOUS STERILIZATION

(75) Inventor: James R. MacNeal, Burton, OH (US)

(73) Assignee: AGA Gas, Inc., Cleveland, OH (US)

( * ) Notice: Subject to any disclaimer, the term of this patent is extended or adjusted under 35 U.S.C. 154(b) by 0 days.

(21) Appl. No.: 09/188,607

(22) Filed: Nov. 9, 1998

(51) Int. Cl.⁷ ........................................ A61L 2/20
(52) U.S. Cl. ................... 422/30; 422/2; 422/34
(58) Field of Search .................. 422/2, 28, 33, 422/34, 30

(56) References Cited

U.S. PATENT DOCUMENTS 5,464,580 * 11/1995 Popescu et al. ..................... 422/34
5,702,669 * 12/1997 Green ................................... 422/30
5,830,409 * 11/1998 Childers et al. ..................... 422/30

* cited by examiner

Primary Examiner—Robert J. Warden, Sr.
Assistant Examiner—Theresa T. Snider
(74) Attorney, Agent, or Firm—Pearne & Gordon LLP

(57) ABSTRACT

A method of removing sterilization gas from a load disposed in a chamber. In accordance with the method, the chamber is evacuated to a subatmospheric pressure. A diffusion gas comprising helium is provided. An amount of the diffusion gas is introduced into the chamber effective to create a superatmospheric diffusion pressure in the chamber. The diffusion gas is allowed to diffuse throughout the chamber to displace sterilization gas from the load. The chamber is evacuated to remove portions of the diffusion gas and the sterilization gas from the chamber.

31 Claims, 2 Drawing Sheets

METHOD FOR REMOVING STERILANT FROM OBJECTS SUBJECTED TO GASEOUS STERILIZATION

BACKGROUND OF THE INVENTION

This invention relates to sterilization in general and, more particularly, to the removal of sterilant from objects subjected to gaseous sterilization.

Gaseous sterilization is an attractive alternative to other methods of sterilization, such as steam sterilization, plasma sterilization, and radiation sterilization, because gaseous sterilization does not utilize high temperatures, corrosive chemicals, or high radiation levels, which can damage objects being sterilized. Because of these favorable qualities, gaseous sterilization is commonly used in hospitals to sterilize medical devices.

In gaseous sterilization, objects to be sterilized are contacted with a gaseous sterilant having good microbiocidal properties. Ethylene oxide (ETO) is the most commonly used gaseous sterilant. ETO has excellent microbiocidal properties, but is extremely volatile and flammable. The National Fire Protection Association (NFPA) has given ETO the highest possible flammability hazard rating under NFPA 704. Since ETO is so volatile and flammable, an inert gas is often mixed with ETO to suppress its flammability. Inert gases that are often mixed with ETO include: carbon dioxide ($CO_2$); nitrogen ($N_2$); chlorofluorocarbons (CFCs), such as dichlorodifluoromethane (CFC-12); hydrochlorofluorocarbons (HCFCs), such as chlorodifluoromethane (HCFC-22), and monochloro-tetrafluorethane, which exists in two isomeric forms, 1-chloro-1,2,2,2-tetrafluoroethane (HCFC-124), 1-chloro-1,1,2,2-tetrafluoroethane (HCFC-124a); and mixtures of the foregoing.

For many years, the most commonly used flammability suppressed ETO mixture was a mixture of 12% ETO and 88% CFC-12 (commonly referred to as the "12/88 mixture"). Due to environmental concerns, however, the use of CFCs is being phased out under the Montreal Protocol. Accordingly, flammability suppressed ETO mixtures using HCFCs are becoming more predominant. An example of such a flammability suppressed ETO mixture using HCFCs is disclosed in U.S. Pat. No. 5,376,333 to Shankland et al., which is incorporated herein by reference. Shankland discloses a suppressed ETO mixture comprising 3 to 13 weight percent ETO and 87 to 97 weight percent of monochlorotetrafluorethane. Another example of a flammability suppressed ETO mixture includes a mixture comprising about 10 weight percent ETO and about 90 weight percent of a mixture of HCFC-124 and HCFC-22.

In a typical gaseous sterilization process utilizing ETO or an ETO mixture as the sterilant, a load to be sterilized is first placed in a sterilization chamber. The chamber is hermetically sealed and a vacuum is drawn to remove air from the chamber. The chamber is heated and water vapor is introduced into the chamber, as needed, to bring the chamber to an optimal relative humidity. The sterilant is then introduced into the chamber. The load is exposed to the sterilant for a sterilization period of time, which is typically between 1 and 6 hours, depending on the concentration of sterilant and the temperature of the chamber.

After the sterilization period of time, the load is aerated to remove the sterilant therefrom. Depending on the construction and capabilities of the sterilizer, the load is either aerated in the chamber or in a separate aerator. If the load is composed of a porous material, such as plastic, or ceramic, the load must be aerated for a prolonged detoxification or aeration period of time. With a material such as polyvinylchloride (PVC), the aeration period of time with current technology is typically between 8 and 24 hours, depending on the intended use of the load. As can be appreciated, such a long period of time is undesirable because the sterilizer and the load cannot be re-used during that period of time.

Methods have been developed to reduce the aeration period of time in ETO sterilization processes. An example of such a method is disclosed in U.S. Pat. No. 4,770,851 to Joslyn, which is incorporated herein by reference. In the Joslyn aeration method, a sterilization chamber containing a load is evacuated to a subatmospheric pressure after a sterilization cycle is complete. Steam is then flushed through the chamber, while the subatmospheric pressure is maintained in the chamber. The chamber is then pressurized with heated air, thereby causing some of the steam to condense on interstices of the load. The chamber is then evacuated again to the subatmospheric pressure, thereby causing the steam to vaporize and carry away residual sterilant from the load.

The Joslyn aeration method is a substantial improvement over conventional aeration methods. Typically, the Joslyn aeration method reduces the aeration period of time for PVC to between 4 and 8 hours, depending on the intended use of the load. This period of time, however, is still substantial, and certain types of materials may be damaged by condensing steam on their interstices.

Based upon the foregoing, there is a need in the art for an improved method of removing sterilization gas from a load. The present invention is directed to such a method.

SUMMARY OF THE INVENTION

It therefore would be desirable, and is an advantage of the present invention, to provide an improved method of removing sterilization gas from a load disposed in a chamber. In accordance with the method, the chamber is evacuated to a subatmospheric pressure. A diffusion gas is provided. An amount of the diffusion gas is introduced into the sterilization chamber. The amount of the diffusion gas is allowed to diffuse throughout the sterilization chamber, thereby causing sterilization gas to diffuse away from the load. Portions of the diffusion gas and sterilization gas are then removed from the sterilization chamber.

In one embodiment of the present invention, the diffusion gas is non-flammable and non-condensible at 0–32 psig. In another embodiment, the diffusion gas comprises helium and the steps of introducing the diffusion gas through removing the diffusion gas are repeated until an acceptable residue level of sterilization gas on the load is attained.

Also provided in accordance with the present invention is a method of sterilizing a load in a sterilization chamber using sterilization gas. In accordance with the method, the load is placed in the sterilization chamber and is exposed to sterilization gas. The sterilization chamber is evacuated to a subatmospheric pressure, thereby removing sterilization gas. A diffusion gas is provided that is selected from the group consisting of helium, hydrogen, nitrogen, argon, and carbon dioxide and mixtures thereof. The diffusion gas is introduced into the sterilization chamber in an amount effective to create a superatmospheric diffusion pressure in the sterilization chamber. The amount of the diffusion gas is allowed to diffuse throughout the sterilization chamber, thereby causing sterilization gas to diffuse away from the load. Portions of the diffusion gas and sterilization gas are then removed from the sterilization chamber.

BRIEF DESCRIPTION OF THE DRAWINGS

The features, aspects, and advantages of the present invention will become better understood with regard to the following description, appended claims, and accompanying drawings where:

DETAILED DESCRIPTION OF THE PREFERRED EMBODIMENTS

It should be noted that in the detailed description which follows, parts are parts by weight and percents are weight percents unless otherwise indicated or apparent. When a preferred range such as 5–25 is given, this means preferably at least 5 and preferably not more than 25. It should also be noted that in order to clearly and concisely disclose the present invention, the drawings may not necessarily be to scale and certain features of the invention may be shown in somewhat schematic form.

Figure 1:
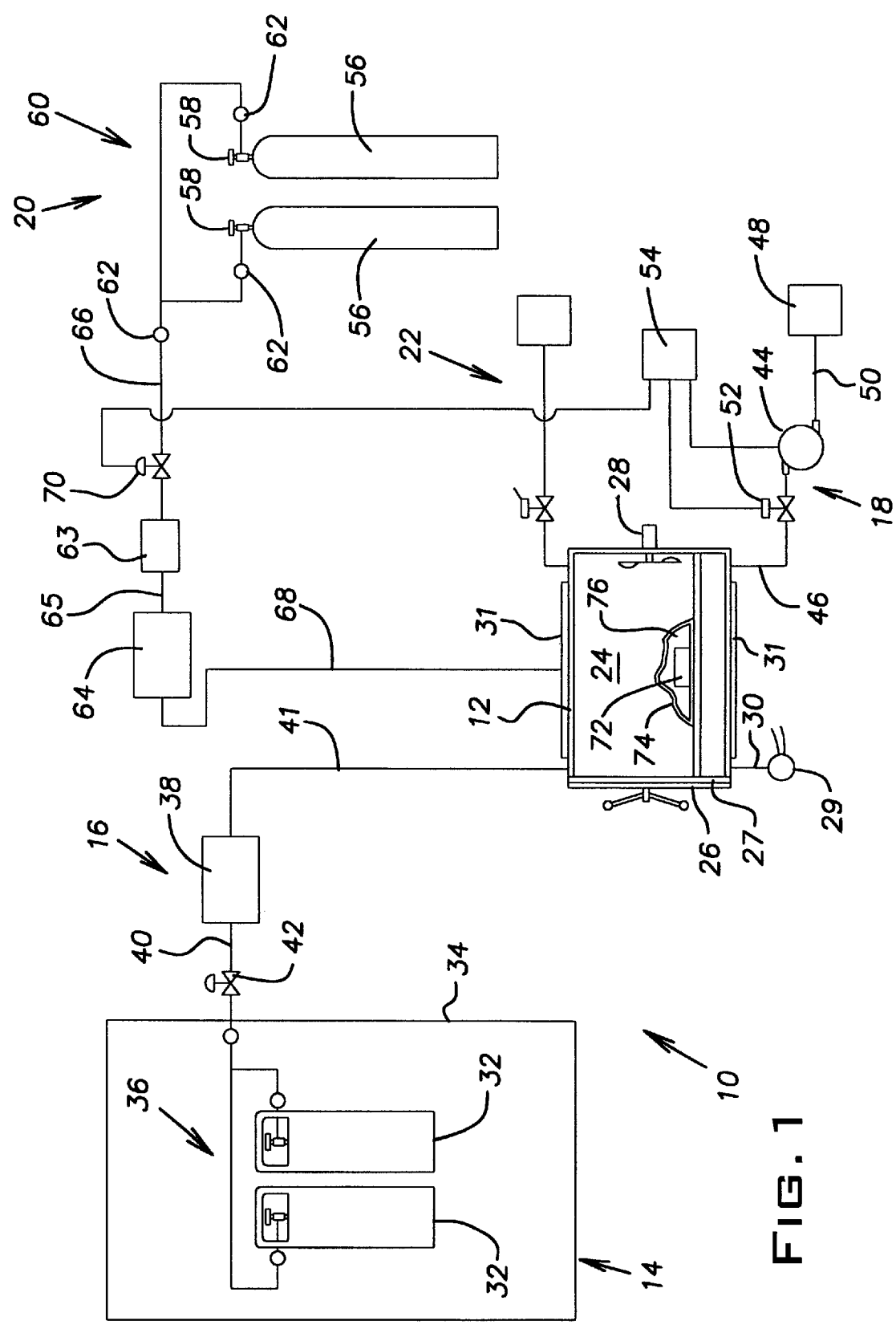
FIG. 1 shows a schematic representation of a sterilization system having an interior chamber.

Referring now to FIG. 1, there is shown a sterilization system 10 wherein the present invention may be practiced. The sterilization system 10 may be a commercially available ETO sterilization system that has been modified to practice the present invention. The sterilization system 10 generally includes a sterilization vessel 12, a sterilant source 14, a sterilant supply system 16, a sterilant removal system 18, and a gas diffusion system 20. The sterilization system 10 may also optionally include a steam supply system 22.

The sterilization vessel 12 is preferably composed of stainless steel and defines an interior chamber 24 having an open end. A door 26 is pivotably mounted to the sterilization vessel 12 and is pivotable between an open position, wherein the door 26 is spaced from the open end, and a closed position, wherein the door 26 covers the open end 24. A conventional lock assembly (not shown) is provided to lock the door 26 in the closed position. The door 26 and the sterilization vessel 12 are provided with seals 27, which cooperate to hermetically seal the open end when the door 26 is locked in the closed position. A circulation fan 28 may be mounted to the sterilization vessel 12 to provide circulation and uniform environmental conditions in the interior chamber 24. A pressure transducer 29 may be connected to the sterilization vessel by a conduit 30.

A heating system is provided to heat the interior chamber 24. The heating system includes a heating device 31 disposed around the exterior of the sterilization vessel 12, and a control device (not shown). The heating device 31 may be an electric resistance heating coil, or other type of heating means, such as a hot water or steam jacket. The control device regulates the flow of electricity or hot water or steam through the heating device 31, or otherwise controls the heating device 31, so as to maintain the interior chamber 24 at a selected temperature.

The sterilant source 14 preferably includes a pair of pressurized tanks 32 for holding a sterilant under pressure. The sterilant may be 100% ETO, the 12/88 mixture, or a mixture of about 8–12% ETO and about 88–92% $CO_2$, or $N_2$. More preferably, the sterilant is a mixture of about 3–13% ETO and about 87–97% HCFC. Still more preferably, the sterilant is a mixture of about 9–12% ETO and about 88–91% monochlorotetrafluoroethane (the "ETO/HCFC-124mixture"). Still more preferably, the sterilant is a mixture of about 10 weight percent ETO and about 90 weight percent of a mixture of HCFC-124 and HCFC-22 (the "ETO/HCFC-124/HCFC-22mixture"), which is available from Allied Signal under the name OXYFUME 2002, and from the Pennsylvania Engineering Company under the name PENNGASS 2.

The tanks 32 are preferably disposed in a sealed enclosure 34 connected to a ventilation system (not shown) that maintains the enclosure 34 at a slightly negative pressure. The tanks 32 are pressurized to maintain the sterilant in liquid form. If the sterilant is the ETO/HCFC-124/HCFC-22mixture, the tanks 32 are pressurized to about 60 psig. Eductor tubes (not shown) are disposed in the tanks 32 to conduct the sterilant from the bottoms of the tanks 32 to a header assembly 36, which connects the tanks 32 to the sterilant supply system 16. The sterilant is supplied from the tanks 32 sequentially such that the sterilant is supplied from only one of the tanks 32 at a time. Preferably, the header assembly 36 is provided with an automatic transfer feature that automatically switches from an exhausted one of the tanks 32 to a filled one of the tanks 32, without interrupting the supply of sterilant.

The sterilant supply system 16 supplies the sterilant from the sterilant source 14 to the sterilization vessel 12. The sterilant supply system 16 includes a vaporizer 38 having an inlet connected to the header assembly 36 by piping 40, and an outlet connected to the sterilization chamber by piping 41. A solenoid valve 42 is disposed in the piping 40 and is operable to control the supply of sterilant to the vaporizer 38 and, thus, the sterilization vessel 12. The vaporizer 38 reduces the pressure of the sterilant and heats the sterilant, thereby causing the sterilant to vaporize into a gas. The vaporizer 38 is controlled such that the temperature of the sterilant gas entering the sterilization vessel 12 is at a predetermined temperature that will not exceed the temperature limit of the load being sterilized.

The steam supply system 22 may be provided to supply steam to the sterilization vessel 12 prior to sterilization in order to raise the humidity in the interior chamber 24 and hydrate microorganisms on the load disposed therein. If the sterilization system 10 is based on an ETO sterilization system obtained from or modified by the Joslyn Sterilizer Corporation, the steam supply system 22 may also be used to remove air from the interior chamber 24 pursuant to an air removal method disclosed in U.S. Pat. No. 4,7,70,851 to Joslyn, referenced earlier. The air removal method of Josyln is similar to the Josyln aeration method described above and utilizes a plurality of alternating steam and pressurized air pulses.

In lieu of using steam to raise the humidity in the interior chamber 24, other conventional humidifying means may be employed. For example, a moisture-releasing device may be placed in the interior chamber 24 along with the load to be sterilized. An example of such a moisture-releasing device is disclosed in U.S. Pat. No. 5,135,715 to Andersen, which is incorporated herein by reference.

Gaseous sterilization with ETO is more effective in killing microorganisms if the microorganisms are hydrated and if the sterilization process is carried out in an atmosphere having at least 30% relative humidity. Thus, the humidifying means chosen should be able to maintain the interior chamber 24 at a relative humidity of at least 30%.

The gas removal system 18 removes gas from the interior chamber 24. The gas removal system 18 includes a vacuum pump 44 having an inlet connected to the sterilization vessel 12 by piping 46, and an outlet connected to a vent 48 by piping 50. A solenoid valve 52 is disposed in the piping 46 and is operable to control the removal of gas from the interior chamber 24. The vacuum pump 44 may be an open water sealed vacuum pump, or more preferably, a dry vacuum pump, or a recycled sealing fluid vacuum pump. Preferably, the operation of the vacuum pump 44 and the solenoid valve 52 is controlled by a programmable controller 54.

In accordance with the present invention, the gas diffusion system 20 cooperates with the gas removal system 18 to remove gaseous sterilant from the interior chamber 24 after sterilization. The gas diffusion system 20 includes at least one tank 56, or more preferably, a pair of tanks 56 of a compressed diffusion gas.

As will become more apparent below, it is desirable for the diffusion gas to have a fast rate of diffusion. The rate of diffusion of a gas is inversely proportional to the square root of its molecular weight. In addition, the rate of diffusion of a gas is proportional to temperature and the negative gradient of the density of the gas. Thus, it is desirable for the diffusion gas to be light, i.e., have as low a molecular weight as possible, and to introduce the diffusion gas at an increased temperature and pressure. It is also preferable if the diffusion gas is not an oxidizer, is unable to support combustion, and is non-flammable. It is further preferable if the diffusion gas is non-condensible at 0–32 psig, more preferably 0–50 psig, and is inert. Since helium is the lightest nonflammable gas, is non-condensible at 0–50 psig, and is inert, the diffusion gas is preferably about 100 percent helium, more preferably 100% United States Pharmacopeia (USP) helium, i.e., medical grade helium. Less preferably, the diffusion gas is a mixture of about 80–90 percent helium and about 10–20 percent hydrogen ($H_2$). Less preferably, the diffusion gas is a mixture of about 51–99 percent helium and about 1–49 percent of a gas selected from the group consisting of hydrogen, nitrogen ($N_2$), argon (Ar), carbon dioxide ($Co_2$), air, and mixtures thereof, wherein the amount of hydrogen present is insufficient to make the diffusion gas flammable, which is about 20 percent or less. Less preferably, the diffusion gas is a mixture of about 1–50 percent helium and about 50–99 percent of a gas selected from the group consisting of hydrogen, nitrogen, argon, carbon dioxide, air, and mixtures thereof, wherein the amount of hydrogen present is insufficient to make the diffusion gas flammable. Less preferably, the diffusion gas is about 50–100 percent nitrogen and about 0–50 percent of a gas selected from the group consisting of hydrogen, argon, carbon dioxide, air, and mixtures thereof, wherein the amount of hydrogen present is insufficient to make the diffusion gas flammable. Less preferably the diffusion gas is a mixture of about 50–100 percent air and about 0–50 percent of a gas selected from the group consisting of hydrogen, argon, carbon dioxide, and mixtures thereof, wherein the amount of hydrogen present is insufficient to make the diffusion gas flammable. Less preferably, the diffusion gas is a mixture of about 50–100 percent $CO_2$ and about 0–50 percent of a gas selected from the group consisting of hydrogen, argon, air, and mixtures thereof, wherein the amount of hydrogen present is insufficient to make the diffusion gas flammable.

If the diffusion gas is helium, the tanks 56 are pressurized to about 2,200 psig. The tanks 56 have conventional outlet assemblies that include shutoff valves 58. The outlet assemblies of the tanks 56 are connected to a header assembly 60 having pressure reducing devices 62. The diffusion gas is supplied from the tanks 56 sequentially such that the diffusion gas is supplied from only one of the tanks 56 at a time. Preferably, the header assembly 60 has an automatic transfer feature that automatically switches from an exhausted one of the tanks 56 to a filled one of the tanks 56, without interrupting the supply of diffusion gas.

The header assembly 60 may be connected by piping 66 to a bioretentive filter 63 that removes any bacteria, viruses, or fungi that may be present in the diffusion gas. An inlet of a heater 64 is connected to the filter 63 by piping 65. An outlet of the heater 64 is connected to the sterilization vessel 12 by piping 68. A solenoid valve 70 is disposed in the piping 66 and is operable to control the flow of the diffusion gas to the filter 63 and, thus, the heater 64 and the interior chamber 24. The operation of the solenoid valve 70 is preferably controlled by the programmable controller 54.

In order to sterilize a load 72 using the sterilization system 10, the load 72 is preferably wrapped, packaged, or otherwise covered with a protective material 74 to form a protected space 76 within which the load 72 is disposed. The protective material 74 may be muslin, paper, plastic or other material specially designed to maintain or preserve the sterility of the load 72 after removal from the sterilization system 10. The load 72 may be pre-packaged with the protective material 74 by the manufacturer of the load 72, or the load 72 may be wrapped or packaged with the protective material 74 at the site where the sterilization system 10 is located.

The door 26 is moved to the open position and the packaged load 72 is placed in the interior chamber 24. The door 26 is then closed and locked. The heating device 31 is activated to heat the interior chamber 24 to a sterilization temperature in a range from about 20° C. to about 100° C. depending upon the nature of the load 72. Preferably, the sterilization temperature is in a range from about 30° C. to about 60° C. more preferably, about 54° C. (130° F.). The relative humidity of the interior chamber 24 is raised above 30 percent, more preferably above 65 percent. Air is removed from the interior chamber 24 before, during or after the humidification. The air is removed by opening the solenoid valve 52 and actuating the vacuum pump 44 until the interior chamber 24 has a vacuum or negative gauge pressure P1 of about 20–25 inches of mercury. If the sterilization system 10 is based on an ETO sterilization system obtained from the Joslyn Sterilizer Corporation, the alternating steam and pressurized air pulses of the Joslyn air removal method may also be employed to remove the air and humidify the interior chamber 24.

The solenoid valve 42 is actuated to cause the sterilant to flow through the piping 40 to the vaporizer 38, where the sterilant is vaporized and heated to the sterilization temperature, which, as set forth above, is preferably about 54° C. The gaseous sterilant flows from the vaporizer 38 into the interior chamber 24 through the piping 41. The gaseous sterilant is admitted into the interior chamber 24 in an amount that preferably produces a pressure P2 in the interior chamber 24, which is greater than atmospheric pressure, i.e., is superatmospheric. Preferably, the pressure P2 is in a range from about 0.1 psig to about 32 psig, more preferably about 12 psig. The load 72 is maintained in the interior chamber 24 for a sterilization period of time, which may be between 1 and 6 hours.

At the conclusion of the sterilization period of time, the sterilant removal method of the present invention is performed to remove the sterilant from the interior chamber 24 and the load 72. Preferably, the sterilant removal method is controlled by the programmable controller 54.

Figure 2:
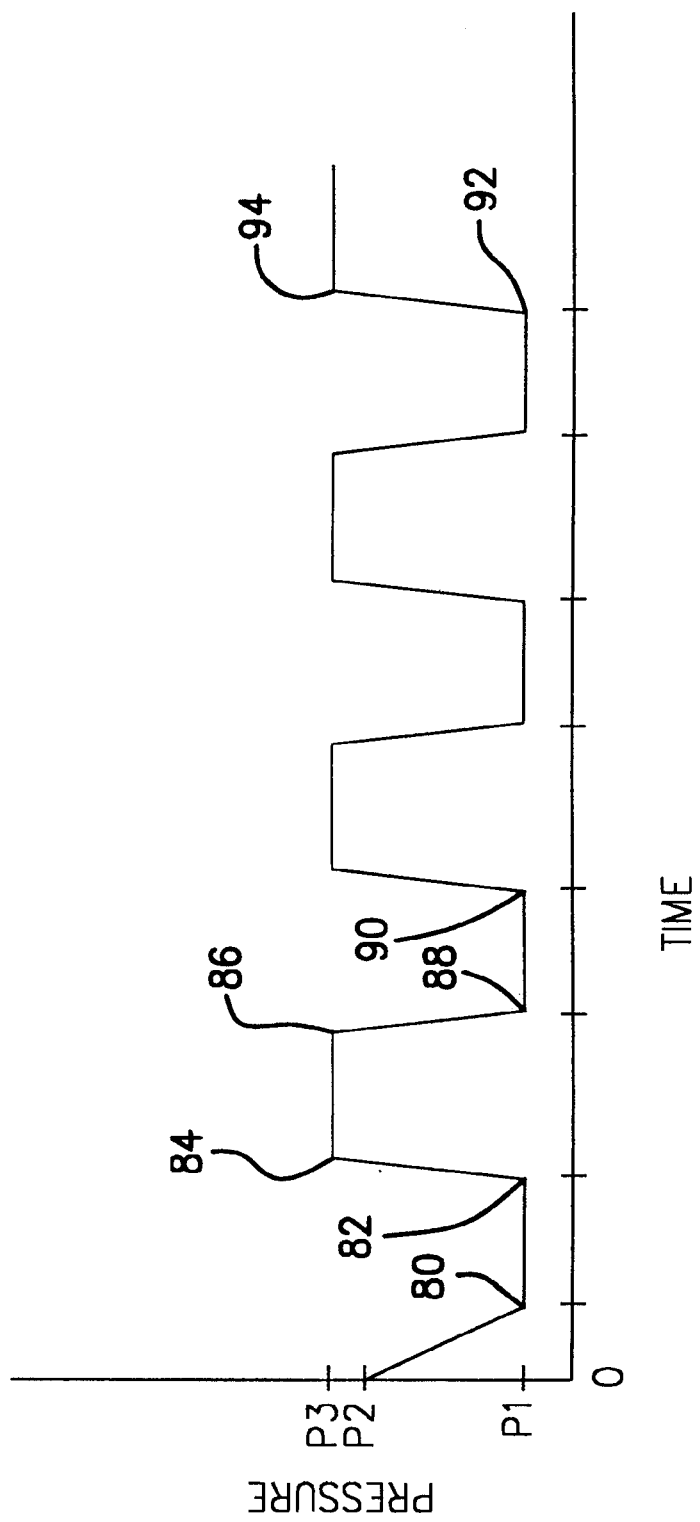
FIG. 2 shows a graphic representation of a process for removing sterilant from a load, with time on the y-axis and pressure of the interior chamber on the x-axis.

Referring now to FIG. 2, the interior chamber 24 is evacuated to the pressure P1 by opening the solenoid valve 52 and actuating the vacuum pump 44. This evacuation is maintained between 80 and 82 and removes most of the gaseous sterilant from the interior chamber 24. At 82, the solenoid valve 52 is closed and the vacuum pump 44 is deactivated.

Referring back to FIG. 1, the solenoid valve 70 is actuated to cause the diffusion gas to flow through the piping 66 to the filter 63 and thence the heater 64, which is activated to heat the diffusion gas to a diffusion temperature T2. Preferably, T2 is above room temperature so as to speed up the diffusion rate of the diffusion gas. Preferably T2 is in a range from about 30° C. to about 70° C., more preferably, about 60° C. (140° F.). The diffusion gas flows from the heater 64 into the interior chamber 24 through the piping 68. The diffusion gas is admitted into the interior chamber 24 until the pressure in the interior chamber 24 reaches a diffusion pressure P3 as shown at 84 of FIG. 2. Preferably, P3 is superatmospheric so as to increase the diffusion rate of the diffusion gas, and is greater than the sterilization pressure P2. Preferably, P3 is in a range from about 0.1 psig to about 50 psig, more preferably in a range from about 5 psig to about 32 psig, more preferably in a range from greater than 12 psig to about 25 psig. Preferably, the heating device 31 is manipulated to maintain the temperature of the interior chamber 24 at the diffusion temperature T2.

The diffusion gas is allowed to diffuse throughout the interior chamber 24. Since the diffusion gas is preferably a light gas, the diffusion gas readily passes through the protective material 74, even if it is composed of plastic. The diffusion gas enters the protected space 76 within which the load 72 is located or disposed and moves into the interstices of the load 72. If permitted, the diffusion gas will continue to diffuse into the protected space 76 and the interstices of the load 72 until the concentration of the diffusion gas is uniform throughout the protected space 76, the interstices of the load 72, and the rest of the interior chamber 24.

In order to maintain a uniform gas concentration throughout the interior chamber 24, the diffusion of the diffusion gas into the protected space 76 and the interstices of the load 72 is accompanied by the diffusion of sterilant out of the interstices of the load 72 and the protected space 76 and into the remaining portion of the interior chamber 24. If permitted, this opposing diffusion of sterilant will continue until the concentration of sterilant is uniform throughout the interior chamber 24, at which point a substantial portion of the sterilant will have been removed from the protected space 76 and the interstices of the load 72.

Referring back to FIG. 2, the foregoing diffusion period is maintained between 84 and 86 to allow the diffusion gas to diffuse into the protected space 76 and the interstices and thereby displace sterilant. At the conclusion of the diffusion period, the solenoid valve 52 is opened and the vacuum pump 44 is actuated to evacuate the interior chamber 24 to the pressure P1 for a period between 88 and 90. The evacuation of the interior chamber 24 removes most of the helium and remaining sterilant from the interior chamber 24.

The process from 82 to 90 is repeated if and until an acceptable sterilant residue level is attained as shown at 92. The duration and number of repetitions of the process may vary based on the use of the load 72 because the acceptable sterilant residue level is dependent upon the use of the load 72. If the load 72 is for contact with skin or mucosa, the acceptable sterilant residue level is about 250 ppm, whereas if the load 72 is for implantation or contact with blood or tissue, the acceptable sterilant residue level is about 25 ppm.

The duration and number of repetitions of the process from 82 to 90 may also vary based on the composition of the load 72 and the protective material 74. The rate of diffusion of a gas is much slower through materials such as plastic (and in particular, PVC) than it is through materials, such as cloth and paper.

When the acceptable sterilant residue level is attained, the pressure of the interior chamber 24 is vented to atmospheric pressure as shown at 94. The load 72 is then removed from the interior chamber 24 and used as needed.

While the invention has been shown and described with respect to a particular embodiment thereof, this embodiment is for the purpose of illustration rather than limitation, and other variations and modifications of the specific embodiment herein described will be apparent to those skilled in the art, all within the intended spirit and scope of the invention. For example, the removal of the residual sterilant from the load 72 using the diffusion gas may be performed in a separate aerator rather than in the sterilization vessel 12.

Accordingly, the invention is not to be limited in scope and effect to the specific embodiment herein described, nor in any other way that is inconsistent with the extent to which the progress in the art has been advanced by the invention.

What is claimed is:

1. A method of removing sterilant from a load disposed in a chamber, said method comprising the steps of:
   evacuating to a subatmospheric pressure a chamber containing a load having sterilant contained therein;
   providing a diffusion gas that is non-flammable and non-condensible at 0–32 psig;
   introducing the diffusion gas into the chamber in an amount effective to create a superatmospheric diffusion pressure in the chamber during a diffusion period;
   allowing the amount of the diffusion gas to diffuse throughout the chamber and the load, thereby causing sterilant to diffuse from within the load and away from the load during the diffusion period with the chamber substantially closed to external flow of diffusion gas; and
   removing portions of the diffusion gas and sterilant from the chamber during an evacuation period.

2. The method of claim 1, wherein the diffusion gas is about 100 weight percent helium.

3. The method of claim 1, wherein the diffusion gas comprises about 80–85 weight percent helium and about 15–20 weight percent hydrogen.

4. The method of claim 1, wherein the diffusion gas comprises about 51–99 weight percent helium and about 1–49 weight percent of a gas selected from the group consisting of hydrogen, nitrogen, argon, carbon dioxide, air, and mixtures thereof.

5. The method of claim 1, wherein the step of removing portions of the diffusion gas and sterilant gas from the chamber comprises evacuating the chamber to the subatmospheric pressure.

6. The method of claim 5, wherein the diffusion pressure is about 5–32 psig.

7. The method of claim 6, further comprising the step of heating the diffusion gas to a diffusion temperature of about 30–70° C.

8. The method of claim 1, wherein the sterilant comprises ethylene oxide.

9. The method of claim 1, further comprising the steps about:
   introducing a second amount of the diffusion gas into the chamber after the step of removing portions of the diffusion gas and sterilant from the chamber; and
   allowing the second amount of the diffusion gas to diffuse throughout the chamber and the load, thereby causing sterilant to diffuse away from the load and removing portions of the diffusion gas and sterilant from the chamber during a second evacuation period.

10. The method of claim 9, wherein said diffusion pressure is about 5–32 psig.

11. The method of claim 1, wherein the step of providing a diffusion gas includes providing a diffusion gas selecting from the group consisting of helium, air and mixtures thereof.

12. The method of claim 11, wherein the steps of introducing diffusion gas to create a superatmospheric pressure and removing portions of the diffusion gas and sterilant are repeated.

13. A method of removing sterilant from a load disposed in a chamber, said method comprising the steps of:

evacuating to a subatmospheric pressure a chamber containing a load having sterilant contained therein;

providing a diffusion gas that is non-flammable and non-condensible at 0–32 psig;

introducing an amount of the diffusion gas into the chamber;

flushing steam through the chamber with heated air; and removing heated air from the chamber by evacuating the chamber to the subatmospheric pressure.

14. The method of claim 13, wherein the steps of flushing with steam, pressurizing with heated air, and removing heated air are performed before the step of introducing the diffusion gas into the chamber.

15. The method of claim 13, wherein the steps of flushing with steam, pressurizing with heated air, and removing heated air are performed after the step of removing portions of the diffusion gas from the chamber.

16. The method of claim 13, further comprising the steps of:

introducing a second amount of the diffusion gas into the chamber after the step of removing portions of the diffusion gas and sterilant from the chamber; and allowing the second amount of the diffusion gas to diffuse throughout the chamber and the load, thereby causing sterilant to diffuse away from the load.

17. The method of claim 13, wherein the subatmospheric pressure is about 20–25 inches of mercury.

18. The method of claim 13, wherein the step of introducing the diffusion gas into the chamber includes introducing an amount effective to create a superatmospheric diffusion pressure in the chamber during a diffusion period.

19. The method of claim 18, wherein said diffusion pressure is about 5–32 psig.

20. A method of sterilizing a load in a sterilization chamber using sterilization gas, said method comprising the steps of:

placing the load in the sterilization chamber;

exposing the load to sterilization gas;

evacuating the sterilization chamber to a subatmospheric pressure, thereby removing sterilization gas;

providing a diffusion gas selected from the group consisting of helium, hydrogen, nitrogen, argon, and carbon dioxide and mixtures thereof;

introducing the diffusion gas into the sterilization chamber in an amount effective to create a superatmospheric diffusion pressure in the sterilization chamber;

allowing the amount of the diffusion gas to diffuse throughout the sterilization chamber and the load, thereby causing sterilization gas to diffuse away from the load; and removing portions of the diffusion gas and sterilization gas from the sterilization chamber.

21. The method of claim 20, wherein the diffusion pressure is in a range from about 0.1 psig to about 50 psig.

22. The method of claim 21, wherein the diffusion pressure is about 5–32 psig.

23. The method of claim 22, further comprising the step of heating the diffusion gas to a diffusion temperature of about 30–70° C.

24. The method of claim 20, wherein the diffusion gas is about 100 weight percent helium.

25. A method of removing sterilant from a load disposed in a chamber, said method comprising the steps of:

(a) evacuating to a subatmospheric pressure a chamber containing a load having sterilant contained therein;

(b) providing a diffusion gas comprising helium;

(c) introducing the diffusion gas into the chamber in an amount effective to create a superatmospheric pressure in the chamber during a diffusion period;

(d) allowing the amount of the diffusion gas to diffuse throughout the chamber and the load, thereby causing sterilant to diffuse from within the load and away from the load during the diffusion period with the chamber substantially closed to external flow of diffusion gas;

(e) removing portions of the diffusion gas and sterilant from the chamber; and (f) repeating steps (c) through (e) until ant acceptable residue level of sterilant is attained.

26. The method of claim 25, wherein the diffusion gas is about 100 weight percent helium.

27. The method of claim 26, wherein the amount of the diffusion gas introduced into the chamber is effective to create a diffusion pressure of about 5–32 psig in the chamber.

28. The method of claim 27, further comprising the step of heating the diffusion gas to a diffusion temperature of about 30–70° C.

29. The method of claim 28, wherein the sterilant comprises a mixture of about 9–12% ethylene oxide and about 88–91% monochlorotetrafluoroethane.

30. The method of claim 28, wherein the sterilant comprises a mixture of about 9–12% ethylene oxide and a mixture of about 88–91% monochlorotetrafluoroethane and chlorodifluoromethane.

31. The method of claim 25, wherein the diffusion gas comprises about 51–99 weight percent helium and about 1–49 weight percent of a gas selected from the group consisting of hydrogen, nitrogen, argon, carbon dioxide, air, and mixtures thereof.

* * * * *

UNITED STATES PATENT AND TRADEMARK OFFICE
CERTIFICATE OF CORRECTION

PATENT NO. : 6,290,906 B1  Page 1 of 1
DATED : September 18, 2001
INVENTOR(S) : MacNeal It is certified that error appears in the above-identified patent and that said Letters Patent is hereby corrected as shown below:

<u>Title page,</u>
Item [56], References Cited, please insert:

| | | | |
|---|---|---|---|
| -- 5,464,580 | 9/1996 | Childers et al. | 442/300 |
| 5,527,508 | 6/1996 | Childers et al. | 422/33 |
| 5,492,672 | 2/1996 | Childers et al. | 422/28 |
| 5,447,684 | 9/1995 | Williams | 422/20 |
| 5,445,792 | 8/1995 | Rickloff et al. | 422/28 |
| 5,376,333 | 12/1994 | Shankland et al. | 422/34 |
| 5,340,538 | 8/1994 | Zaikow et al. | 422/33 |
| 5,238,035 | 2/1994 | Karthaus et al. | 422/31 |
| 5,227,132 | 7/1993 | Andersen et al. | 422/2 |
| 5,160,700 | 11/1992 | Andersen | 422/34 |
| 5,128,101 | 7/1992 | Boynton | 422/31 |
| 5,118,471 | 6/1992 | Andersen et al. | 422/34 |
| 5,082,636 | 1/1992 | Andersen | 422/294 |
| 5,041,264 | 8/1991 | Williams | 422/28 |
| 5,019,344 | 5/1991 | Kutner et al. | 422/21 |
| 4,971,761 | 11/1990 | Johnson | 422/34 |
| 4,943,414 | 9/1990 | Jacobs et al. | 422/28 |
| 4,822,563 | 4/1989 | Joslyn | 422/31 |
| 4,770,851 | 9/1989 | Joslyn | 422/26 |
| 4,410,492 | 10/1983 | Kaye | 422/27 |
| 4,337,223 | 6/1982 | Kaye | 422/112 |
| 3,815,315 | 6/1974 | Glick | 53/425 |
| 3,761,224 | 9/1973 | Ernst | 422/3 |

Signed and Sealed this

Thirteenth Day of August, 2002

Attest:

JAMES E. ROGAN
Attesting Officer  Director of the United States Patent and Trademark Office